United States Patent
Gleave et al.

(10) Patent No.: US 7,935,832 B2
(45) Date of Patent: May 3, 2011

(54) PYRROLE AND ISOINDOLE CARBOXAMIDE DERIVATIVES AS P2X7 MODULATORS

(75) Inventors: Robert James Gleave, Harlow (GB); David George Hubert Livermore, Harlow (GB); Daryl Simon Walter, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/532,868

(22) PCT Filed: Mar. 20, 2008

(86) PCT No.: PCT/EP2008/053343
§ 371 (c)(1), (2), (4) Date: Feb. 18, 2010

(87) PCT Pub. No.: WO2008/116814
PCT Pub. Date: Oct. 2, 2008

(65) Prior Publication Data
US 2010/0210705 A1  Aug. 19, 2010

(30) Foreign Application Priority Data
Mar. 27, 2007  (GB) .................................. 0705882.9

(51) Int. Cl.
*C07D 209/44* (2006.01)
*C07D 207/24* (2006.01)
*C07D 213/02* (2006.01)
*C07D 401/06* (2006.01)
*A61K 31/44* (2006.01)
*A61K 31/40* (2006.01)

(52) U.S. Cl. .................. 548/537; 548/472; 546/277.1; 546/278.4; 514/339; 514/343; 514/416; 514/423

(58) Field of Classification Search .................. None
See application file for complete search history.

(56) References Cited

U.S. PATENT DOCUMENTS

| 2005/0026916 A1 | 2/2005 | Shum et al. | 514/235.5 |
| 2008/0009541 A1 | 1/2008 | Chambers et al. | 514/423 |

FOREIGN PATENT DOCUMENTS

| WO | WO 99/29661 | 6/1999 |
| WO | WO2008/003697 | 1/2008 |

OTHER PUBLICATIONS

Kato et al., *Yakugaku Zasshi*, vol. 92, No. 12, pp. 1507-1514 (1972).

*Primary Examiner* — Kamal A Saeed
*Assistant Examiner* — Nyeemah Grazier
(74) *Attorney, Agent, or Firm* — Duke M. Fitch; Kathryn L. Sieburth; John L. Lemanowicz

(57) ABSTRACT

The present invention relates to a compound of formula (I) or a pharmaceutically acceptable salt thereof:

wherein: $R^2$ represents hydrogen, halogen, $C_{1-6}$ alkyl, $C_{6-10}$ arylmethyl-, $C_{2-6}$ alkenyl, $C_{2-6}$ alkynyl or $C_{3-6}$ cycloalkylmethyl-; and any of said $C_{1-6}$ alkyl, $C_{6-10}$ arylmethyl-, $C_{2-6}$ alkenyl, $C_{2-6}$ alkynyl or $C_{3-6}$ cycloalkylmethyl- is optionally substituted with 1, 2 or 3 halogen atoms; and $R^3$ represents hydrogen, fluorine or methyl;

or $R^2$ and $R^3$ together with the carbon atoms to which they are attached form a benzene ring optionally substituted with 1, 2 or 3 substituents, which may be the same or different, selected from the group consisting of $C_{1-6}$ alkyl, $C_{2-6}$ alkenyl and $C_{2-6}$ alkynyl.

The compounds or salts modulate P2X7 receptor function and are capable of antagonizing the effects of ATP at the P2X7 receptor. The invention also provides the use of such compounds or salts, or pharmaceutical compositions thereof, in the treatment of disorders mediated by the P2X7 receptor, for example pain, inflammation or neurodegeneration.

16 Claims, No Drawings

PYRROLE AND ISOINDOLE CARBOXAMIDE DERIVATIVES AS P2X7 MODULATORS

This application is a 371 of International Application No. PCT/EP2008/053343, filed Mar. 20, 2008, which claims the priority of Great Britain Application No. GB0705882.9, filed Mar. 27, 2007, which are incorporated herein in their entirety.

The present invention relates to heterocyclic amide derivatives which modulate P2X7 receptor function and are capable of antagonizing the effects of ATP at the P2X7 receptor ("P2X7 receptor antagonists"); to processes for their preparation; to pharmaceutical compositions containing them; and to the use of such compounds in therapy.

The P2X7 receptor is a ligand-gated ion-channel which is expressed in cells of the hematopoietic lineage, e.g. macrophages, microglia, mast cells, and lymphocytes (T and B) (see, for example, Collo, et al. Neuropharmacology, Vol. 36, pp 1277-1283 (1997)), and is activated by extracellular nucleotides, particularly adenosine triphosphate (ATP). Activation of P2X7 receptors has been implicated in giant cell formation, degranulation, cytolytic cell death, CD62L shedding, regulation of cell proliferation, and release of proinflammatory cytokines such as interleukin 1 (IL-1β) and tumour necrosis factor (TNFα) (e.g. Hide, et al. Journal of Neurochemistry, Vol 75., pp 965-972 (2000)). P2X7 receptors are also located on antigen presenting cells, keratinocytes, parotid cells, hepatocytes, erythrocytes, erythroleukaemic cells, monocytes, fibroblasts, bone marrow cells, neurones, and renal mesangial cells. Furthermore, the P2X7 receptor is expressed by presynaptic terminals in the central and peripheral nervous systems and has been shown to mediate glutamate release in glial cells (Anderson, C. et al. Drug. Dev. Res., Vol. 50, page 92 (2000)).

The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders. Preclinical in vivo studies have directly implicated the P2X7 receptor in both inflammatory and neuropathic pain (Dell'Antonio et al., Neurosci. Lett., 327, pp 87-90, 2002. Chessell, I P., et al., Pain, 114, pp 386-396, 2005) while there is in vitro evidence that P2X7 receptors mediate microglial cell induced death of cortical neurons (Skaper, S. D., et al., Program No. 937.7. 2005 *Abstract Viewer/Itinerary Planner*. Washington, D.C.: Society for Neuroscience, 2005. Online). In addition, up-regulation of the P2X7 receptor has been observed around β-amyloid plaques in a mouse model of Alzheimer's disease (Parvathenani, L. et al. J. Biol. Chem., Vol. 278(15), pp 13309-13317, 2003). T. Kato and M. Sato, *Yakugaku Zasshi*, 1972, 92(12), 1507-1514 discloses N-benzyl-1-benzyl-3-methyl-5-oxo-3-pyrroline-2-carboxamide as compound (VIIId).

The present invention provides compounds which modulate P2X7 receptor function and are capable of antagonizing the effects of ATP at the P2X7 receptor (P2X7 receptor antagonists). A first aspect of the present invention provides a compound of formula (I) or a pharmaceutically acceptable salt thereof:

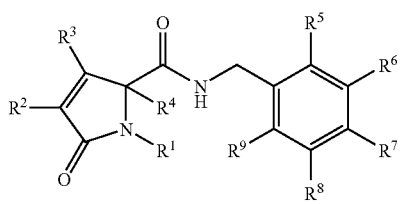

(I)

wherein:
$R^1$ represents $C_{1-6}$ alkyl, $C_{2-6}$ alkenyl, $C_{2-6}$ alkynyl, $C_{3-6}$ cycloalkyl, $C_{3-6}$ cycloalkylmethyl- or pyridinylmethyl-, any of which is optionally substituted with 1, 2 or 3 halogen atoms; or unsubstituted phenyl or benzyl; and
either $R^2$ represents hydrogen, halogen, $C_{1-6}$ alkyl, $C_{6-10}$ arylmethyl-, $C_{2-6}$ alkenyl, $C_{2-6}$ alkynyl or $C_{3-6}$ cycloalkylmethyl-; and any of said $C_{1-6}$ alkyl, $C_{6-10}$ arylmethyl-, $C_{2-6}$ alkenyl, $C_{2-6}$ alkynyl or $C_{3-6}$ cycloalkylmethyl- is optionally substituted with 1, 2 or 3 halogen atoms;
and $R^3$ represents hydrogen, fluorine or methyl;
or $R^2$ and $R^3$ together with the carbon atoms to which they are attached form a benzene ring optionally substituted with 1, 2 or 3 substituents, which may be the same or different, selected from the group consisting of $C_{1-6}$ alkyl, $C_{2-6}$ alkenyl and $C_{2-6}$ alkynyl;
and
$R^4$ represents hydrogen, fluorine or methyl; and
$R^5$, $R^6$, $R^7$, $R^8$ and $R^9$ independently represent hydrogen, halogen (e.g. fluorine or chlorine), cyano, $C_{1-6}$ alkyl, $C_{2-6}$ alkenyl, $C_{2-6}$ alkynyl, $C_{3-6}$ cycloalkyl or phenyl, and any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms; or $R^8$ and $R^9$ together with the carbon atoms to which they are attached form a benzene ring which is optionally substituted with 1, 2 or 3 halogen atoms;
with the proviso that when $R^5$ and $R^9$ are both selected from hydrogen or fluorine, at least one of $R^6$, $R^7$ and $R^8$ is a halogen atom.

As used herein, the term "alkyl" (when used as a group or as part of a group) refers to a straight or branched hydrocarbon chain containing the specified number of carbon atoms. For example, $C_{1-6}$ alkyl means a straight or branched hydrocarbon chain containing at least 1 and at most 6 carbon atoms. Examples of alkyl include, but are not limited to; methyl (Me), ethyl (Et), n-propyl, i-propyl, n-hexyl and i-hexyl.

As used herein, the term "alkenyl" refers to a straight or branched hydrocarbon chain containing the specified number of carbon atoms wherein at least one carbon-carbon bond is a double bond. Examples of alkenyl include, but are not limited to ethenyl, propenyl, n-butenyl, i-butenyl, n-pentenyl and i-pentenyl.

As used herein, the term "alkynyl" refers to a straight or branched hydrocarbon chain containing the specified number of carbon atoms wherein at least one carbon-carbon bond is a triple bond. Examples of alkynyl include, but are not limited to ethynyl, propynyl, butynyl, i-pentynyl, n-pentynyl, i-hexynyl and n-hexynyl.

The term 'cycloalkyl' unless otherwise stated means a closed 3 to 6 membered non-aromatic ring, for example cyclopropyl, cyclobutyl, cyclopentyl or cyclohexyl.

The term 'aryl' as used herein refers to a $C_{6-10}$ monocyclic or bicyclic hydrocarbon ring wherein at least one ring is aromatic. Examples of such groups include phenyl and naphthyl.

The term 'halogen' is used herein to describe, unless otherwise stated, a group selected from fluorine, chlorine, bromine or iodine.

It is to be understood that the present invention covers and discloses all possible combinations of particular, preferred, suitable, or other embodiments of groups (e.g. of $R^1$, $R^2$, $R^3$, $R^4$, $R^5$, $R^6$, $R^7$, $R^8$ and/or $R^9$), e.g. all possible combinations of embodiments of different groups, which embodiments are described herein.

In certain particular embodiments of the invention, $R^1$ represents $C_{1-6}$ alkyl, $C_{2-6}$ alkenyl, $C_{3-6}$ cycloalkyl or pyridinylmethyl-, any of which is optionally substituted with 1, 2 or 3 halogen atoms; or unsubstituted phenyl or benzyl.

In a particular embodiment, $R^1$ represents unsubstituted $C_{1-6}$ alkyl, $C_{2-6}$ alkenyl, $C_{2-6}$ alkynyl, $C_{3-6}$ cycloalkyl, pyridinylmethyl-, phenyl or benzyl. In a more particular embodiment, $R^1$ represents unsubstituted $C_{1-4}$ alkyl, $C_{3-5}$ cycloalkyl, pyridinylmethyl-, phenyl or benzyl.

Preferably, $R^1$ represents methyl or ethyl. More preferably, $R^1$ represents methyl.

In one particular embodiment of the invention, $R^2$ represents hydrogen, halogen, $C_{1-6}$ alkyl, $C_{6-10}$ arylmethyl-, $C_{2-6}$ alkenyl, $C_{2-6}$ alkynyl or $C_{3-6}$ cycloalkylmethyl-.

In a more particular embodiment, $R^2$ represents hydrogen or methyl. In a still more particular embodiment, $R^2$ represents hydrogen.

In one particular embodiment of the invention, $R^3$ represents hydrogen or methyl. In a more particular embodiment, $R^3$ represents methyl.

In an alternative embodiment of the invention, $R^2$ and $R^3$ together with the carbon atoms to which they are attached form a benzene ring optionally substituted with 1, 2 or 3 (e.g. 1 or 2) substituents, which may be the same or different, selected from the group consisting of $C_{1-6}$ alkyl, $C_{2-6}$ alkenyl and $C_{2-6}$ alkynyl. In this case, in a particular embodiment, $R^2$ and $R^3$ together with the carbon atoms to which they are attached form a benzene ring optionally substituted with 1, 2 or 3 (e.g. 1 or 2) substituents, which may be the same or different, and which are $C_{1-4}$ alkyl (e.g. methyl or ethyl, such as methyl). In this case, in a more particular embodiment, $R^2$ and $R^3$ together with the carbon atoms to which they are attached form an unsubstituted benzene ring.

In a particular embodiment of the invention, either $R^2$ represents hydrogen or methyl (e.g. hydrogen) and $R^3$ represents hydrogen or methyl (e.g. methyl); or $R^2$ and $R^3$ together with the carbon atoms to which they are attached form an unsubstituted benzene ring. In a more particular embodiment, $R^2$ and $R^3$ together with the carbon atoms to which they are attached form an unsubstituted benzene ring.

In a particular embodiment of the invention, $R^4$ represents hydrogen or methyl. In a more particular embodiment, $R^4$ represents hydrogen.

In one particular embodiment of the invention, $R^5$, $R^6$, $R^7$, $R^8$ and $R^9$ independently represent hydrogen, halogen (e.g. fluorine or chlorine), cyano, trifluoromethyl or unsubstituted $C_{1-6}$ alkyl; or $R^8$ and $R^9$ together with the carbon atoms to which they are attached form an unsubstituted benzene ring. In a more particular embodiment, $R^5$, $R^6$, $R^7$, $R^8$ and $R^9$ independently represent hydrogen, halogen (e.g. fluorine or chlorine), methyl or trifluoromethyl. In a yet more particular embodiment, $R^5$, $R^6$, $R^7$, $R^8$ and $R^9$ independently represent hydrogen, chlorine, fluorine, bromine, methyl or trifluoromethyl; such as hydrogen, chlorine, fluorine, methyl or trifluoromethyl.

In one particular embodiment of the invention, there is provided a compound of formula (I), or a pharmaceutically acceptable salt thereof, wherein:
$R^1$ represents unsubstituted $C_{1-4}$ alkyl, $C_{2-4}$ alkenyl, $C_{3-5}$ cycloalkyl, pyridinylmethyl-, phenyl or benzyl (in particular wherein $R^1$ represents methyl or ethyl);
$R^2$ and $R^3$ represent hydrogen or methyl, or $R^2$ and $R^3$ together with the carbon atoms to which they are attached form an unsubstituted benzene ring; and
$R^5$, $R^6$, $R^7$, $R^8$ and $R^9$ independently represent hydrogen, chlorine, fluorine, bromine, methyl or trifluoromethyl.

Preferably, $R^1$ represents methyl or ethyl (e.g. methyl);

$R^2$ and $R^3$ represent hydrogen or methyl, or $R^2$ and $R^3$ together with the carbon atoms to which they are attached form an unsubstituted benzene ring; and
$R^5$, $R^6$, $R^7$, $R^8$ and $R^9$ independently represent hydrogen, chlorine, fluorine, bromine, methyl or trifluoromethyl.

In all embodiments of the invention herein described, when $R^5$ and $R^9$ are both selected from hydrogen or fluorine, at least one of $R^6$, $R^7$ and $R^8$ is a halogen atom.

In a particular embodiment of the invention herein described, when $R^5$ and $R^9$ are both selected from hydrogen or fluorine, at least one of $R^6$, $R^7$ and $R^8$ is a halogen atom, and not more than one of $R^6$, $R^7$ and $R^8$ is a $CF_3$ group.

A particular aspect of the invention provides a compound selected from examples E1 to E7, as shown and/or named below.

A preferred aspect of the invention provides: N-{[2-chloro-3-(trifluoromethyl)phenyl]methyl}-2-ethyl-3-oxo-2,3-dihydro-1H-isoindole-1-carboxamide

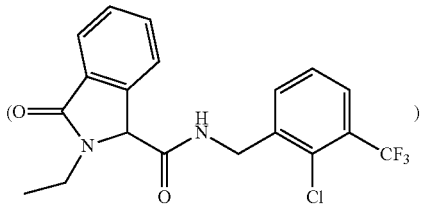

(e.g. see E4), or N-[(2,4-dichlorophenyl)methyl]-2-methyl-3-oxo-2,3-dihydro-1H-isoindole-1-carboxamide

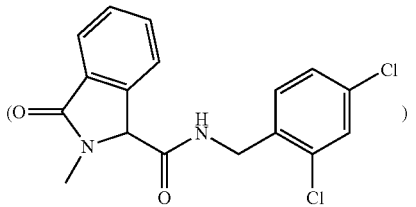

(e.g. see E5), or N-{[2-chloro-3-(trifluoromethyl)phenyl]methyl}-2-methyl-3-oxo-2,3-dihydro-1H-isoindole-1-carboxamide

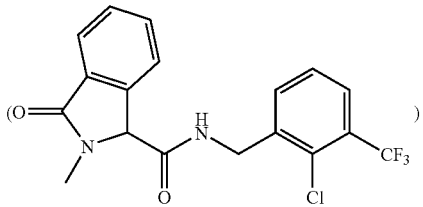

(e.g. see E7).

Antagonists of P2X7 may be useful in preventing, treating, or ameliorating a variety of pain states (e.g. neuropathic pain, chronic inflammatory pain, and visceral pain), inflammation and neurodegeneration, in particular Alzheimer's disease. P2X7 antagonists may also constitute useful therapeutic agents in the management of rheumatoid arthritis and inflammatory bowel disease.

Compounds or salts of the present invention which modulate P2X7 receptor function and are capable of antagonizing the effects of ATP at the P2X7 receptor ("P2X7 receptor antagonists") may be competitive antagonists, inverse agonists, or negative allosteric modulators of P2X7 receptor function.

Certain compounds of formula (I) may in some circumstances form acid addition salts thereof. It will be appreciated that for use in medicine compounds of formula (I) may be used as salts, in which case the salts should be pharmaceutically acceptable.

Pharmaceutically acceptable salts include those described by Berge, Bighley and Monkhouse, J. Pharm. Sci., 1977, 66, 1-19. When a compound of the present invention is basic, pharmaceutically acceptable salts (in the case of acid addition salts) are in one embodiment prepared from pharmaceutically acceptable acids, including inorganic and organic acids, e.g. by admixture of the compound and the acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In a particular embodiment, the pharmaceutically acceptable acid is benzenesulfonic, camphorsulfonic, ethanesulfonic, hydrobromic, hydrochloric, methanesulfonic, nitric, phosphoric, sulfuric, or p-toluenesulfonic acid.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The compounds of formula (I) or salts thereof may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Compounds of formula (I) or salts thereof are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. In the examples given herein, the composition of the final product has not been characterised and thus the stereochemistry of the final product has not been indicated. However, the chirality of the main component of the product mixture will be expected to reflect that of the starting material and the enantiomeric excess will depend on the synthetic method used and is likely to be similar to that of an analogous example (where such an example exists). Compounds or salts made in one chiral form are thus expected to be able to be prepared in the alternative chiral form using the appropriate starting material. Alternatively, if racemic starting materials are used, it would be expected that a racemic product would be produced and the single enantiomers could be separated by the usual methods. The invention also extends to any tautomeric forms and mixtures thereof.

The subject invention also includes isotopically-labeled compounds or salts, which are identical to those recited in formula (I) and following, but for the fact that one or more atoms are replaced by an atom having an atomic mass or mass number different from the atomic mass or mass number most commonly found in nature. Examples of isotopes that can be incorporated into compounds or salts of the invention include isotopes of hydrogen, carbon, nitrogen, oxygen, phosphorous, fluorine, iodine, and chlorine, such as 3H, 11C, 14C, 18F, 123I and 125I.

Compounds of the present invention and pharmaceutically acceptable salts of said compounds that contain the aforementioned isotopes and/or other isotopes of other atoms are within the scope of the present invention. Isotopically-labeled compounds or salts of the present invention, for example those into which radioactive isotopes such as 3H, 14C are incorporated, are potentially useful in drug and/or substrate tissue distribution assays. Tritiated, i.e., 3H, and carbon-14, i.e., 14C, isotopes are particularly preferred for their ease of preparation and detectability. 11C and 8F isotopes are particularly useful in PET (positron emission tomography), and 125I isotopes are particularly useful in SPECT (single photon emission computerized tomography). PET and SPECT are useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labeled compounds of formula (I) or salts thereof and following of this invention are in one embodiment prepared by carrying out the procedures disclosed in the Schemes and/or in the Examples below, by substituting a readily available isotopically labeled reagent for a non-isotopically labeled reagent.

A further aspect of the invention provides a compound of formula (I) or a pharmaceutically acceptable salt thereof which is not a radioactive isotopically labeled compound or salt. In a particular embodiment, the compound or salt is not an isotopically labeled compound or salt.

Preparation of Compounds

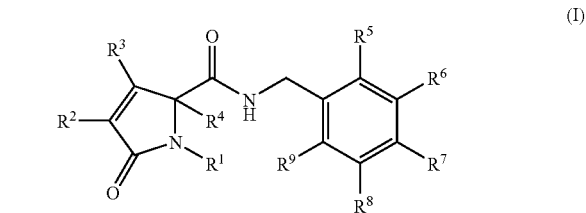

(I)

Compounds of formula (I), wherein the variables are as defined above, and salts and solvates thereof may be prepared by the methodology described hereinafter, constituting a further aspect of this invention.

According to a further aspect of the invention, there is provided a process for preparing a compound of formula (I) or a pharmaceutically acceptable salt thereof which comprises:
(a) Coupling of a carboxylic acid of formula (2) (or an activated derivative thereof) with an amine of formula (3) (see Scheme 1), wherein $R^1$, $R^2$, $R^3$, $R^4$, $R^5$, $R^6$, $R^7$, $R^8$, and $R^9$ are as defined above. Compounds (2) and (3) are optionally protected.
(b) Treatment of a compound of formula (4) with a suitable salt, such as lithium chloride, and a suitable base, such as triethylamine, in a suitable solvent such as tetrahydrofuran and at a suitable temperature such as between 0° C. and room temperature (see Scheme 2), wherein $R^1$, $R^2$, $R^3$, $R^4$, $R^5$, $R^6$, $R^7$, $R^8$, and $R^9$ are as defined above. Compound (4) is optionally protected.
(c) Deprotecting a compound of formula (I) which is protected. Examples of protecting groups and the means for their removal can be found in T. W. Greene and P. G. M. Wuts 'Protective Groups in Organic Synthesis' (J. Wiley and Sons, 3$^{rd}$ Ed. 1999).
(d) Interconversion of compounds of formula (I) to other compounds of formula (I). Examples of conventional interconversion procedures include epimerisation, oxidation, reduction, alkylation, aromatic substitution, nucleophilic substitution, amide coupling and ester hydrolysis.

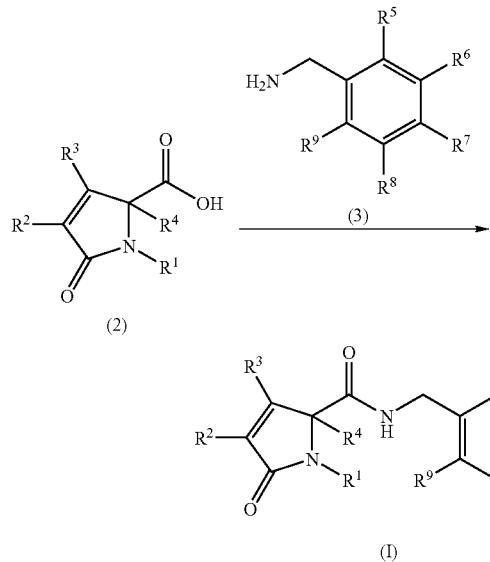

The coupling of an acid of formula (2) and an amine of formula (3) typically comprises the use of activating agents, such as N-(3-dimethylaminopropyl)-N'-ethylcarbodiimide hydrochloride, or polymer-supported carbodiimide, 1-hydroxybenzotriazole (HOBT) or 1-Hydroxy-7-azabenzotriazole (HOAt), and optionally a suitable base such as a tertiary alkylamine (e.g. diisopropylethylamine, N-ethyl morpholine, triethylamine) or pyridine, in a suitable solvent such as DMF and/or dichloromethane and at a suitable temperature e.g. between 0° C. and room temperature. Alternatively the coupling of (2) and (3) may be accomplished by treatment with O-(7-Azabenzotriazol-1-yl)-N,N,N',N'-tetramethyluronium hexafluorophosphate and a suitable tertiary alkylamine such as diisopropylethylamine in a suitable solvent such as dimethylformamide at a suitable temperature such as room temperature. Alternatively, the compound of formula (2) may be employed as an activated derivative (e.g. acid chloride, mixed anhydride, active ester (e.g. O-acyl-isourea)), and under such circumstances process (a) typically comprises treatment of said activated derivative with an amine (Ogliaruso, M. A.; Wolfe, J. F. in *The Chemistry of Functional Groups* (Ed. Patai, S.) *Suppl. B: The Chemistry of Acid Derivatives, Pt.* 1 (John Wiley and Sons, 1979), pp 442-8; Beckwith, A. L. J. in *The Chemistry of Functional Groups* (Ed. Patai, S.) *Suppl. B: The Chemistry of Amides* (Ed. Zabricky, J.)(John Wiley and Sons, 1970), pp 73 ff).

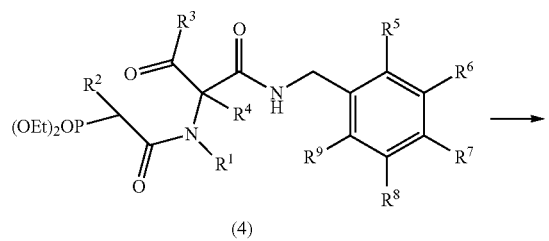

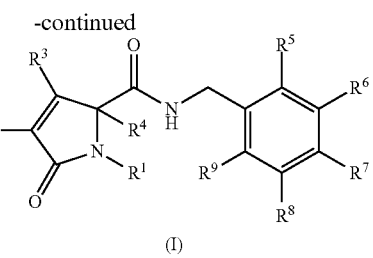

Representative methods for the preparation of compounds of formula (2) and (4) are shown in Schemes 3-4 below:

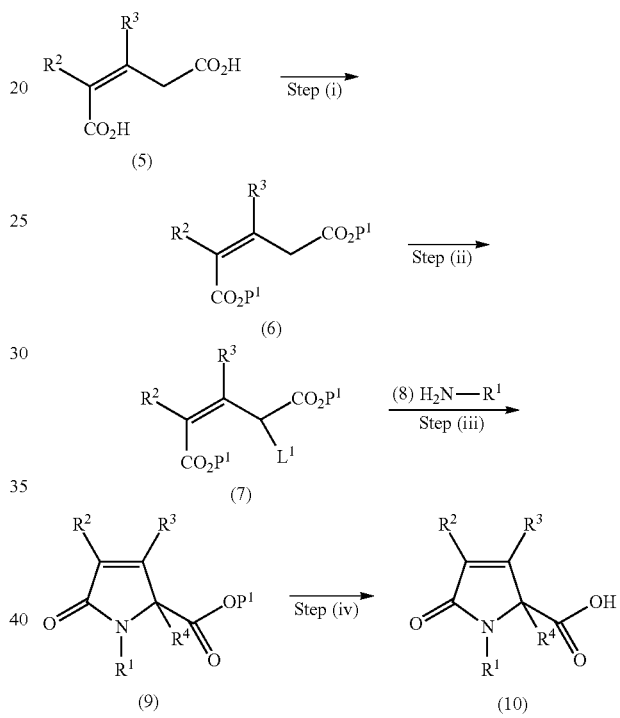

wherein $R^1$, $R^2$, $R^3$, and $R^4$ are as defined above, and $R^2$ and $R^3$ together form a benzene ring, and $P^1$ represents a suitable protecting groups such as $C_{1-6}$ alkyl and $L^1$ represents a suitable leaving group such as a halide.

Step (i) typically comprises treatment of (5) with an alcohol such as ethanol and an acid such as concentrated sulphuric acid in a suitable solvent such as toluene at a suitable temperature such as between room temperature and 120° C.

Step (ii) typically comprises treatment of (6) with a halogen such as bromine and irradiation with a lamp, such as a 120 W Tungsten bulb, in a suitable solvent such as chloroform at a suitable temperature such as between room temperature and reflux temperature.

Step (iii) typically comprises treatment of (7) with an amine (8) in a suitable solvent such as tetrahydrofuran at a suitable temperature such as room temperature.

Deprotection step (iv) typically comprises a standard procedure for conversion of a carboxylic ester to an acid, such as use of an appropriate hydroxide salt (e.g. sodium hydroxide) in an appropriate solvent such as a mixture of ethanol and water at a suitable temperature such as between 0° C. and room temperature.

Scheme 4.

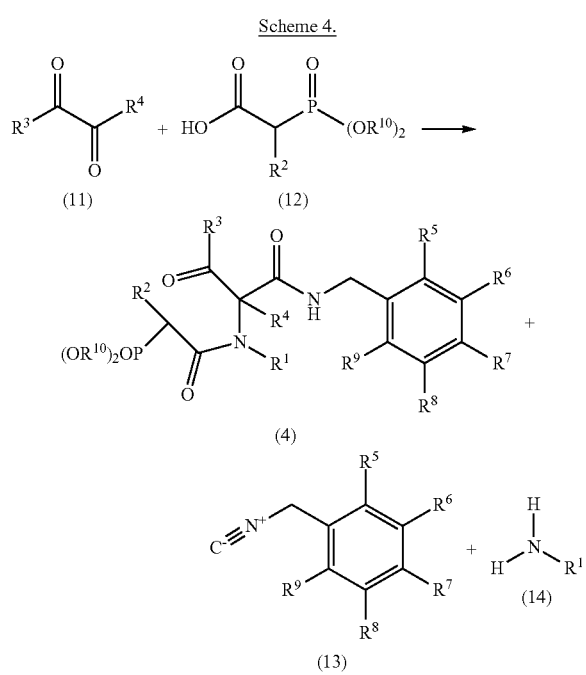

wherein $R^1$, $R^2$, $R^3$, $R^4$, $R^5$, $R^6$, $R^7$, $R^8$, and $R^9$ are as defined above (excluding the cases where $R^2$ and $R^3$ form a benzene ring), and $R^{10}$ represents a suitable group such as $C_{1-6}$ alkyl.

The reaction typically comprises stirring a mixture of a dicarbonyl compound of formula (11), a bis(alkyloxy)phosphoryl acetic acid of formula (12) an isocyanide of formula (13) and an amine of formula (14) in a suitable solvent such as methanol at a suitable temperature such as between room temperature and 160° C. Compounds (13) and (14) are optionally protected. Processes analogous to this have been described previously in the chemical literature (e.g. H. Tye, and M. Whittaker, Org. Biomol. Chem., 2004, 2, 813-815; G. C. B. Harriman WO 9900362 A1).

Compounds of the general formulae (5), (8), (11), (12), (13) and (14) are typically either available from commercial sources or can be prepared by a person skilled in the art using methods described in the chemical literature (or using analogous methods).

Where relevant, pharmaceutically acceptable salts may be prepared conventionally by reaction with the appropriate acid or acid derivative.

Clinical Indications

It is believed that, as compounds or pharmaceutically acceptable salts of the present invention modulate P2X7 receptor function and are capable of antagonizing the effects of ATP at the P2X7 receptor, they may be useful in the treatment of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

Chronic articular pain conditions include rheumatoid arthritis, osteoarthritis, rheumatoid spondylitis, gouty arthritis and juvenile arthritis.

Pain associated with functional bowel disorders includes non-ulcer dyspepsia, non-cardiac chest pain and irritable bowel syndrome.

Neuropathic pain syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions which could potentially be treated by compounds of the present invention include fever, inflammation, immunological diseases, abnormal platelet function diseases (e.g. occlusive vascular diseases), impotence or erectile dysfunction; bone disease characterised by abnormal bone metabolism or resorbtion; hemodynamic side effects of non-steroidal anti-inflammatory drugs (NSAID's) and cyclooxygenase-2 (COX-2) inhibitors, cardiovascular diseases; neurodegenerative diseases and neurodegeneration, neurodegeneration following trauma, tinnitus, dependence on a dependence-inducing agent such as opioids (e.g. morphine), CNS depressants (e.g. ethanol), psychostimulants (e.g. cocaine) and nicotine; complications of Type I diabetes, kidney dysfunction, liver dysfunction (e.g. hepatitis, cirrhosis), gastrointestinal dysfunction (e.g. diarrhoea), colon cancer, overactive bladder and urge incontinence. Depression and alcoholism could potentially also be treated by compounds of the present invention.

Inflammatory conditions include skin conditions (e.g. sunburn, burns, eczema, dermatitis, allergic dermatitis, psoriasis), meningitis, ophthalmic diseases such as glaucoma, retinitis, retinopathies, uveitis and of acute injury to the eye tissue (e.g. conjunctivitis), inflammatory lung disorders (e.g. asthma, bronchitis, emphysema, allergic rhinitis, respiratory distress syndrome, pigeon fancier's disease, farmer's lung, chronic obstructive pulmonary disease (COPD), airways hyperresponsiveness); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation and other conditions with an inflammatory component such as vascular disease, migraine, periarteritis nodosa, thyroiditis, aplastic anaemia, Hodgkin's disease, sclerodoma, myaesthenia gravis, multiple sclerosis, sarcoidosis, nephrotic syndrome, Bechet's syndrome, gingivitis, myocardial ischemia, pyrexia, systemic lupus erythematosus, polymyositis, tendinitis, bursitis, and Sjogren's syndrome.

Immunological diseases include autoimmune diseases, immunological deficiency diseases or organ transplantation.

Bone diseases characterised by abnormal bone metabolism or resorbtion include osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis.

Cardiovascular diseases include hypertension or myocardiac ischemia; atherosclerosis; functional or organic venous insufficiency; varicose therapy; haemorrhoids; and shock states associated with a marked drop in arterial pressure (e.g. septic shock).

Neurodegenerative diseases include dementia, particularly degenerative dementia (including senile dementia, dementia with Lewy bodies, Alzheimer's disease, Pick's disease, Huntingdon's chorea, Parkinson's disease and Creutzfeldt-Jakob disease, Amyotrophic Lateral Sclerosis (ALS) and motor neuron disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment associated with ageing, particularly Age Associated Memory Impairment.

The compounds of formula (I) or pharmaceutically acceptable salts thereof may also be useful for neuroprotection and in the treatment of neurodegeneration following trauma such as stroke, cardiac arrest, pulmonary bypass, traumatic brain injury, spinal cord injury or the like.

The compounds or pharmaceutically acceptable salts of the present invention may also be useful in the treatment of malignant cell growth and/or metastasis, and myoblastic leukaemia.

Complications of Type 1 diabetes include diabetic microangiopathy, diabetic retinopathy, diabetic nephropathy, macular degeneration, glaucoma, nephrotic syndrome, aplastic anaemia, uveitis, Kawasaki disease and sarcoidosis.

Kidney dysfunction includes nephritis, glomerulonephritis, particularly mesangial proliferative glomerulonephritis and nephritic syndrome.

It is to be understood that reference to treatment includes both treatment of established symptoms and prophylactic treatment, unless explicitly stated otherwise.

According to a further aspect of the invention, we therefore provide a compound of formula (I) or a pharmaceutically acceptable salt thereof for use in therapy and/or for use in human or veterinary medicine.

According to another aspect of the invention, we provide a compound of formula (I) or a pharmaceutically acceptable salt thereof for use in the treatment or prevention (e.g. treatment) of a condition which is mediated by P2X7 receptors, for example a condition or disease disclosed herein (in particular pain, inflammation or a neurodegenerative disease, more particularly pain such as inflammatory pain, neuropathic pain or visceral pain), e.g. in a mammal such as a human or rodent e.g. human or rat e.g. human.

According to a further aspect of the invention, we provide a method of treating a human or animal (e.g. rodent e.g. rat) subject suffering from a condition which is mediated by P2X7 receptors, for example a condition or disease disclosed herein (in particular pain, inflammation or a neurodegenerative disease, more particularly pain such as inflammatory pain, neuropathic pain or visceral pain), which comprises administering to said subject an effective amount of a compound of formula (I) or a pharmaceutically acceptable salt thereof.

According to a further aspect of the invention we provide a method of treating a human or animal (e.g. rodent e.g. rat) subject, for example a human subject, suffering from pain, inflammation, an immunological disease, a bone disease or a neurodegenerative disease, which method comprises administering to said subject an effective amount of a compound of formula (I) or a pharmaceutically acceptable salt thereof.

According to a yet further aspect of the invention we provide a method of treating a human or animal (e.g. rodent e.g. rat) subject, for example a human subject, suffering from inflammatory pain, neuropathic pain or visceral pain which method comprises administering to said subject an effective amount of a compound of formula (I) or a pharmaceutically acceptable salt thereof.

According to a further aspect of the invention we provide a method of treating a subject, for example a human subject, suffering from Alzheimer's disease which method comprises administering to said subject an effective amount of a compound of formula (I) or a pharmaceutically acceptable salt thereof.

According to another aspect of the invention, we provide the use of a compound of formula (I) or a pharmaceutically acceptable salt thereof for the manufacture of a medicament for the treatment or prevention (e.g. treatment) of a condition which is mediated by the action of P2X7 receptors, for example a condition or disease disclosed herein (in particular pain, inflammation or a neurodegenerative disease, more particularly pain such as inflammatory pain, neuropathic pain or visceral pain), e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prevention (e.g. treatment) of pain, inflammation, an immunological disease, a bone disease or a neurodegenerative disease (in particular pain, inflammation or a neurodegenerative disease, more particularly pain such as inflammatory pain, neuropathic pain or visceral pain), e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prevention (e.g. treatment) of inflammatory pain, neuropathic pain or visceral pain, e.g. in a mammal such as a human or rodent e.g. human or rat e.g. human.

In one aspect of the invention we provide the use of a compound of formula (I) or a pharmaceutically acceptable salt thereof for the manufacture of a medicament for the treatment or prevention (e.g. treatment) of Alzheimer's disease, e.g. in a mammal such as a human or rodent e.g. human or rat e.g. human.

In order to use a compound of formula (I) or a pharmaceutically acceptable salt thereof for the treatment of humans and other mammals it is normally formulated in accordance with standard pharmaceutical practice as a pharmaceutical composition. Therefore in another aspect of the invention there is provided a pharmaceutical composition comprising a compound of formula (I), or a pharmaceutically acceptable salt thereof, adapted for use in human or veterinary medicine.

In order to use the compounds of formula (I) or the pharmaceutically acceptable salts thereof in therapy, they will normally be formulated into a pharmaceutical composition in accordance with standard pharmaceutical practice.

The present invention also provides a pharmaceutical composition, which comprises a compound of formula (I), or a pharmaceutically acceptable salt thereof, and optionally a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are for example prepared utilising a compound of the invention or pharmaceutically acceptable salt thereof and a sterile vehicle. In one particular embodiment the compound or salt, depending on the vehicle and concentration used, is either suspended or dissolved in the vehicle. In preparing solutions, the compound or salt can e.g. be dissolved for injection and filter sterilised before filling into a suitable vial or ampoule and sealing. In one embodiment, adjuvants such as a local anaesthetic, preservatives and buffering agents are dissolved in the vehicle. To enhance the stability, the composition can for example be frozen after filling into the vial and the water removed under vacuum. Parenteral suspensions are typically prepared in substantially the same manner, except that the compound or salt is typically suspended in the vehicle instead of being dissolved, and sterilization cannot readily be accomplished by filtration. The compound or salt can be sterilised e.g. by exposure to ethylene oxide before suspension in a sterile vehicle. In a particular embodiment, a surfactant or wetting agent is included in the composition to facilitate uniform distribution of the compound.

In one embodiment, the composition contains from 0.1% to 99% by weight, in particular from 10 to 60% by weight, of the active material (the compound or salt of the invention), e.g. depending on the method of administration.

The dose of the compound or salt used in the treatment of the aforementioned disorders will vary in the usual way with the seriousness of the disorders, the weight of the sufferer, and/or other similar factors. However, as a general guide, a unit dose of 0.05 to 1000 mg, for example 0.05 to 200 mg, such as 20 to 40 mg, of the compound or salt of the invention (measured as the compound) may be used. In one embodiment, such unit doses are for administration once a day e.g. to a mammal such as a human; alternatively such unit doses may be for administration more than once (e.g. twice) a day e.g. to a mammal such as a human. Such therapy may extend for a number of weeks or months.

Compounds of formula (I) or salts thereof may be used in combination with other therapeutic agents, for example medicaments which are or may be useful in the treatment of the above mentioned disorders.

Suitable examples of other such therapeutic agents may include a β2-agonist (also known as β2 adrenoceptor agonists; e.g. formoterol) and/or a corticosteroid (e.g. budesonide, fluticasone (e.g. as propionate or furoate esters), mometasone (e.g. as furoate), beclomethasone (e.g. as 17-propionate or 17,21-dipropionate esters), ciclesonide, triamcinolone (e.g. as acetonide), flunisolide, rofleponide and butixocort (e.g. as propionate ester), for the treatment of respiratory disorders (such as asthma and chronic obstructive pulmonary disease (COPD)) as described in WO 2007/008155 and WO 2007/008157.

A further therapeutic agent may include a 3-hydroxy-3-methylglutaryl coenzyme A (HMG CoA) reductase inhibitor (e.g. atorvastatin, fluvastatin, lovastatin, pravastatin, rosuvastatin, and simvastatin) for the treatment of cardiovascular disorders (such as atherosclerosis) as described in WO 2006/083214.

A further therapeutic agent may include a non-steroid anti-inflammatory drug (NSAID; e.g. ibuprofen, naproxen, aspirin, celecoxib, diclofenac, etodolac, fenoprofen, indomethacin, ketoprofen, ketorolac, oxaprozin, nabumetone, sulindac, tolmetin, rofecoxib, valdecoxib, lumaricoxib, meloxicam, etoricoxiband and parecoxib) for the treatment of an inflammatory disease or disorder (such as rheumatoid arthritis or osteoarthritis) as described in WO 2005/025571.

A further therapeutic agent may include a tumour necrosis factor α (TNFα) inhibitor (e.g. Etanercept or an anti-TNFα antibody such as Infliximab and Adalimumab) for the treatment of an inflammatory disease or disorder (such as rheumatoid arthritis or osteoarthritis) as described in WO 2004/105798.

A further therapeutic agent may include 2-hydroxy-5-[[4-[(2-pyridinylamino)sulfonyl]phenyl]azo]benzoic acid (sulfasalazine) for the treatment of an inflammatory disease or disorder (such as rheumatoid arthritis) as described in WO 2004/105797.

A further therapeutic agent may include N-[4-[[(2,4-diamino-6-pteridinyl)methyl]methylamino]benzoyl]-L-glutamic acid (methotrexate) for the treatment of an inflammatory disease or disorder (such as rheumatoid arthritis) as described in WO 2004/105796.

A further therapeutic agent may include an inhibitor of pro TNFα convertase enzyme (TACE) for the treatment of an inflammatory disease or disorder (such as rheumatoid arthritis) as described in WO 2004/073704.

A further therapeutic agent may include:
a) sulfasalazine;
b) a statin, such as atorvastatin, lovastatin, pravastatin, simvastatin, fluvastatin, cerivastatin, crilvastatin, dalvastatin, rosuvastatin, tenivastatin, fluindostatin, velostatin, dalvastatin, nisvastatin, bervastatin, pitavastatin, rivastatin, glenvastatin, eptastatin, tenivastatin, flurastatin, rosuvastatin or itavastatin;
c) a glucocorticoid agent, such as dexamethasone, methylprednisolone, prednisolone, prednisone and hydrocortisone;
d) an inhibitor of p38 kinase;
e) an anti-IL-6-receptor antibody;
f) anakinra;
g) an anti-IL-1 monoclonal antibody;
h) an inhibitor of JAK3 protein tyrosine kinase;
i) an anti-macrophage colony stimulation factor (M-CSF) monoclonal antibody; or
j) an anti-CD20 monoclonal antibody, such as rituximab, PRO70769, HuMax-CD20 (Genmab AJS), AME-133 (Applied Molecular Evolution), or hA20 (Immunomedics, Inc.) for the treatment of an IL-1 mediated disease (such as rheumatoid arthritis) as described in WO 2006/003517.

When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone.

The following Descriptions and Examples illustrate the preparation of compounds of the invention but are not intended to be limiting.

EXAMPLES

Example 1

1-cyclopropyl-N-[(2,4-dichlorophenyl)methyl]-3-methyl-5-oxo-2,5-dihydro-1H-pyrrole-2-carboxamide (E1)

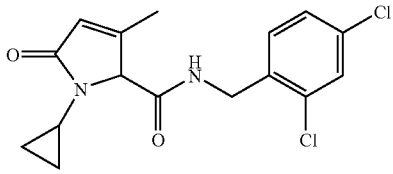

To a solution of diethyl (2-{cyclopropyl[1-({[(2,4-dichlorophenyl)methyl]amino}-carbonyl)-2-oxopropyl]amino}-2-oxoethyl)phosphonate (0.043 g, 0.087 mmol, prepared as described below) in anhydrous tetrahydrofuran (2.5 ml) at 0° C. was added lithium chloride (0.016 g, 0.39 mmol). The mixture was stirred until all of the lithium chloride dissolved and then triethylamine (0.066 ml, 0.87 mmol) was added. The mixture was allowed to warm to room temperature and stirred for 18 hrs. Evaporation of the solvent in vacuo and purification of the resulting residue by mass-directed automated HPLC gave 1-cyclopropyl-N-[(2,4-dichlorophenyl)methyl]-3-methyl-5-oxo-2,5-dihydro-1H-pyrrole-2-carboxamide (0.012 g) as a white solid.

LC/MS [M+H]$^+$=339/341, retention time=2.43 minutes.

The diethyl (2-{cyclopropyl[1-({[(2,4-dichlorophenyl)methyl]amino}-carbonyl)-2-oxopropyl]-2-oxoethyl)phosphonate used in the above procedure can be prepared as follows:

To a solution of methylglyoxal (0.153 ml, 1 mmol) in methanol (2 ml) was added cyclopropylamine (0.069 ml, 1 mmol). After stirring at 22° C. for 5 minutes the mixture was treated with [bis(ethyloxy)phosphoryl]acetic acid (0.161 ml, 1 mmol) and (2,4-dichlorophenyl)methyl isocyanide (0.188 g, 1 mmol). The mixture was then stirred for a further 18 hrs at 22° C. following which the solvent was removed in vacuo and the resulting residue was purified by mass-directed automated HPLC to give diethyl (2-{cyclopropyl[1-({[(2,4-dichlorophenyl)methyl]amino}-carbonyl)-2-oxopropyl]amino}-2-oxoethyl)phosphonate (0.043 g) as a brown gum.

LC/MS [M+H]$^+$=493/495, retention time=3.14 minutes.

Example 2

N-[(2,4-dichlorophenyl)methyl]-2-ethyl-3-oxo-2,3-dihydro-1H-isoindole-1-carboxamide (E2)

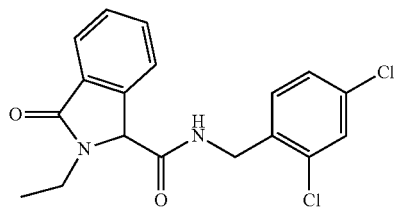

2-Ethyl-3-oxo-2,3-dihydro-1H-isoindole-1-carboxylic acid (0.061 g, 0.3 mmol, prepared as described below) was dissolved in anhydrous dimethylformamide (5 ml) and to this was added 1-hydroxybenzotriazole (0.045 g, 0.3 mmol), diisopropylethylamine (0.105 ml, 0.6 mmol), [(2,4-dichlorophenyl)methyl]amine (0.054 g, 0.3 mmol) and O-(7-azabenzotriazol-1-yl)-N,N,N',N'-tetramethyluronium hexafluorophosphate (0.114 g, 0.3 mmol). The mixture was stirred for 3 hrs and then left to stand overnight. The mixture was diluted with water (50 ml) and a little saturated aqueous sodium chloride solution and extracted with ethyl acetate (3×20 ml). The organic fractions were combined and washed with 10% aqueous sodium carbonate (50 ml) and then with saturated aqueous sodium chloride solution (50 ml), dried over magnesium sulphate and evaporated to give a gum. The gum was purified by mass-directed automated HPLC to give N-[(2,4-dichlorophenyl)methyl]-2-ethyl-3-oxo-2,3-dihydro-1H-isoindole-1-carboxamide (0.056 g).

LC/MS [M+H]$^+$=363, retention time=2.76 minutes.

The 2-Ethyl-3-oxo-2,3-dihydro-1H-isoindole-1-carboxylic acid used in the above procedure can be prepared as follows:

(i) A mixture of homophthalic acid [(2-carboxyphenyl)acetic acid] (5 g, 28 mmol), ethanol (23 ml), toluene (12 ml) and concentrated sulphuric acid (0.5 ml) was heated at reflux, using a Dean-Stark apparatus to remove water formed during the reaction, for 6 hrs and then overnight. The mixture was cooled to 20° C., diluted with toluene (~50 ml) and washed with saturated aqueous sodium hydrogen carbonate solution (~50 ml). The aqueous layer was separated and extracted with more toluene (~50 ml) and then the combined toluene washings were washed with saturated aqueous sodium chloride solution and then dried over magnesium sulphate and evaporated. The resulting yellow oil was purified by automated flash silica-gel column chromatography (using a Biotage SP4), eluting with 0-25% gradient of ethyl acetate in hexane (10 column volumes) and then with a 25-50% gradient of ethyl acetate in hexane (2 column volumes), to give ethyl 2-[2-(ethyloxy)-2-oxoethyl]benzoate (5.9 g) as a pale yellow oil.

LC/MS [M+H]$^+$=237, retention time=2.93 minutes.

(ii) A solution of ethyl 2-[2-(ethyloxy)-2-oxoethyl]benzoate (4.15 g, 17.5 mmol) in chloroform (70 ml) was treated with bromine (1.3 ml, 25 mmol) and stirred at reflux, whilst irradiating with a 120 W tungsten bulb, for 5 hrs. The mixture was cooled to 20° C., evaporated and purified by automated flash silica-gel column chromatography (using a Biotage SP4), eluting with 0-10% gradient of ethyl acetate in hexane (10 column volumes), to give ethyl 2-[1-bromo-2-(ethyloxy)-2-oxoethyl]benzoate (2.77 g) as a pale yellow oil.

LC/MS retention time=3.24 minutes.

(iii) A solution of ethyl 2-[1-bromo-2-(ethyloxy)-2-oxoethyl]benzoate (2.11 g, 6.7 mmol) in anhydrous tetrahydrofuran (200 ml) was treated with a 2M solution of ethylamine in tetrahydrofuran (8 ml, 16 mmol) and stirred at 20° C. for 48 hrs. The tetrahydrofuran was removed by evaporation and then the residue was taken up in ethyl acetate (150 ml) and water (150 ml). The aqueous phase was separated and extracted with more ethyl acetate (100 ml) and then the combined organic fractions was washed with saturated aqueous sodium chloride solution (150 ml) and then dried over magnesium sulphate and evaporated to give a yellow oil. The oil was purified by automated flash silica-gel column chromatography (using a Biotage SP4), eluting with 10-50% gradient of ethyl acetate in hexane, to give ethyl 2-ethyl-3-oxo-2,3-dihydro-1H-isoindole-1-carboxylate (1.4 g) as a colourless oil which solidified on standing and was used in the next step without further purification.

LC/MS [M+H]$^+$=234, retention time=2.33 minutes.

(iv) A solution of ethyl 2-ethyl-3-oxo-2,3-dihydro-1H-isoindole-1-carboxylate (0.283 g, 1.2 mmol) in ethanol (6 ml) and water (6 ml) was treated with 2M aqueous sodium hydroxide solution (0.6 ml) and stirred at 20° C. for 1.5 hrs. Starting material was still evident at this stage so a further aliquot of 2M aqueous sodium hydroxide solution (0.8 ml) was added and stirring continued for a further 4 hrs. The mixture was evaporated to remove the ethanol and the aqueous residue was diluted with water (40 ml), washed with diethyl ether (25 ml), then acidified to pH2 using 2M aqueous hydrogen chloride, and extracted with dichloromethane (4×25 ml). The organic extracts were combined, filtered through a hydrophobic frit, and evaporated to give 2-ethyl-3-oxo-2,3-dihydro-1H-isoindole-1-carboxylic acid as a white solid (0.255 g) which was used without further purification.

LC/MS [M+H]$^+$=206, retention time=1.48 minutes.

Examples 3-7

In a manner analogous to that described for Example 2 above the compounds tabulated below (Table 1) were prepared by substituting the appropriate amine (or salt thereof) for the [(2,4-dichlorophenyl)methyl]amine used in the above procedure. All of the amines used in Table 1 are available from commercial sources or can be prepared using routes described previously in the chemical literature unless stated otherwise, In addition, in the cases of examples 5-7, methylamine was substituted for the ethylamine used in step (iii) of the procedure described above.

TABLE 1

| Example no. | Chemical name | [M + H]$^+$ | Retention time (mins) |
|---|---|---|---|
| E3 | 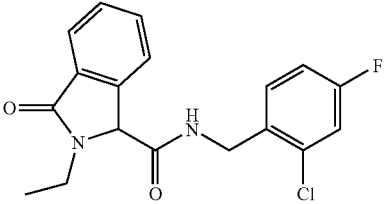<br>N-[(2-chloro-4-fluorophenyl)methyl]-2-ethyl-3-oxo-2,3-dihydro-1H-isoindole-1-carboxamide | 347 | 2.56 |
| E4 | 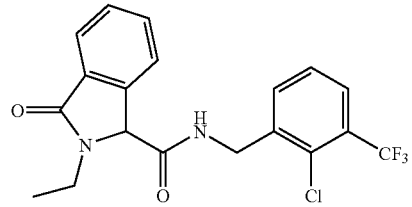<br>N-{[2-chloro-3-(trifluoromethyl)phenyl]methyl}-2-ethyl-3-oxo-2,3-dihydro-1H-isoindole-1-carboxamide | 397 | 2.81 |
| E5 | 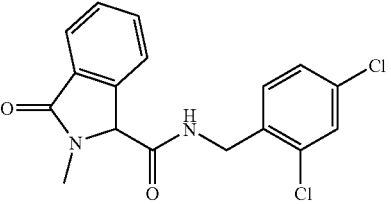<br>N-[(2,4-dichlorophenyl)methyl]-2-methyl-3-oxo-2,3-dihydro-1H-isoindole-1-carboxamide | 349 | 2.63 |

TABLE 1-continued

| Example no. | Chemical name | [M + H]+ | Retention time (mins) |
|---|---|---|---|
| E6 |  N-[(2-chloro-4-fluorophenyl)methyl]-2-methyl-3-oxo-2,3-dihydro-1H-isoindole-1-carboxamide | 333 | 2.43 |
| E7 | 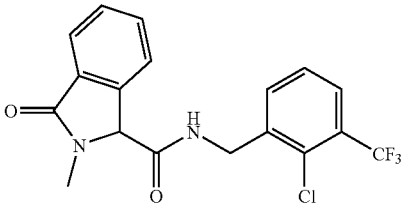 N-{[2-chloro-3-(trifluoromethyl)phenyl]methyl}-2-methyl-3-oxo-2,3-dihydro-1H-isoindole-1-carboxamide | 383 | 2.69 |

Mass-Directed Automated HPLC

Where indicated in the above examples, purification by mass-directed automated HPLC was carried out using the following apparatus and conditions:

Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
Waters MassLynx version 4 SP2
Column The columns used are Waters Atlantis, the dimensions of which are 19 mm×100 mm (small scale) and 30 mm×100 mm (large scale). The stationary phase particle size is 5 μm.

Solvents
A: Aqueous solvent=Water+0.1% Formic Acid
B: Organic solvent=Acetonitrile+0.1% Formic Acid
Make up solvent=Methanol: Water 80:20
Needle rinse solvent=Methanol
Methods There are five methods used depending on the analytical retention time of the compound of interest. They have a 13.5-minute runtime, which comprises a 10-minute gradient followed by a 3.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow Rate

All of the above methods have a flow rate of either 20 mls/min (Small Scale) or 40 mls/min (Large Scale).

Liquid Chromatography/Mass Spectrometry

Analysis of the above Examples by Liquid Chromatography/Mass Spectrometry (LC/MS) was carried out using the following apparatus and conditions:

Hardware
Agilent 1100 Gradient Pump
Agilent 1100 Autosampler
Agilent 1100 DAD Detector
Agilent 1100 Degasser
Agilent 1100 Oven
Agilent 1100 Controller
Waters ZQ Mass Spectrometer
Sedere Sedex 85
Software
Waters MassLynx version 4.0 SP2
Column The column used is a Waters Atlantis, the dimensions of which are 4.6 mm×50 mm. The stationary phase particle size is 3 μm.

Solvents
A: Aqueous solvent=Water+0.05% Formic Acid
B: Organic solvent=Acetonitrile+0.05% Formic Acid
Method The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

The above method has a flow rate of 3 ml/mins.

The injection volume for the generic method is 5 ul.

The column temperature is 30 deg.

The UV detection range is from 220 to 330 nm.

Pharmacological Data

Compounds of the invention may be tested for in vitro biological activity at the P2X7 receptor in accordance with the following studies:

Ethidium Accumulation Assay

Studies were performed using NaCl assay buffer of the following composition (in mM): 140 mM NaCl, HEPES 10, N-methyl-D-glucamine 5, KCl 5.6, D-glucose 10, $CaCl_2$ 0.5 (pH 7.4). HEK293 cells, expressing human recombinant P2X7 receptors, were grown in poly-L-lysine pretreated 96 well plates for 18-24 h. (The cloning of the human P2X7 receptor is described in U.S. Pat. No. 6,133,434). The cells were washed twice with 350 µl of assay buffer before addition of 50 µl of antagonist. The cells were then incubated at room temperature (19-21° C.) for 30 min before addition of ATP and ethidium (100 µM final assay concentration). The ATP concentration was chosen to be close to the $EC_{80}$ for the receptor type and was 1 mM for studies on the human P2X7 receptor. Incubations were continued for 8 or 16 min and were terminated by addition of 25 µl of 1.3M sucrose containing 5 mM of the P2X7 receptor antagonist reactive black 5 (Aldrich). Cellular accumulation of ethidium was determined by measuring fluorescence (excitation wavelength of 530 nm and emission wavelength of 620 nm) from below the plate with a Canberra Packard Fluorocount (Pangbourne, UK). Antagonist $pIC_{50}$ values for blocking ATP responses were determined using iterative curve fitting techniques.

Fluorescent Imaging Plate Reader (FLIPR) Ca Assay

Studies were performed using NaCl assay buffer of the following composition (in mM) for human P2X7: 137 NaCl; 20 HEPES; 5.37 KCl; 4.17 $NaHCO_3$; 1 $CaCl_2$; 0.5 $MgSO_4$; and 1 g/L of D-glucose (pH 7.4).

HEK293 cells, expressing human recombinant P2X7 receptors, were grown in poly-L-lysine pretreated 384 well plates for 42-48 h. (The cloning of the human P2X7 receptor is described in U.S. Pat. No. 6,133,434). The cells were washed three times with 80 µl of assay buffer, loaded for 1 h at 37° C. with 2 µM Fluo4 (Teflabs), washed three times again, and left with 30 µl buffer before the addition of 10 µl of 4× concentrated antagonist. The cells were then incubated at room temperature for 30 mins before addition (online, by FLIPR384 or FLIPR3 instrument (Molecular Devices)) of Benzoylbenzoyl-ATP (BzATP) 60 µM final assay concentration. The BzATP concentration was chosen to be close to the $EC_{80}$ for the receptor type. Incubations and reading were continued for 90 sec, and intracellular calcium increase was determined by measuring fluorescence (excitation wavelength of 488 nm and emission wavelength of 516 nm) from below the plate, with FLIPR CCD camera. Antagonist $pIC_{50}$ values for blocking BzATP responses were determined using iterative curve fitting techniques.

The compounds of Examples 1-7 were tested in the FLIPR Ca Assay and/or the Ethidium Accumulation Assay for human P2X7 receptor antagonist activity and found to have pIC50 values>4.7 in the FLIPR Ca Assay and/or pIC50 values>5.5 in the Ethidium Accumulation Assay. The compounds of Examples 1, 2, 4, 5, 6 and 7 were found to have pIC50 values of about 6.2 or more in the Ethidium Accumulation Assay. The compounds of Examples 4, 5 and 7 were found to have pIC50 values of about 6.9 or more in the Ethidium Accumulation Assay.

The invention claimed is:

1. A compound of formula (I), or a pharmaceutically acceptable salt thereof:

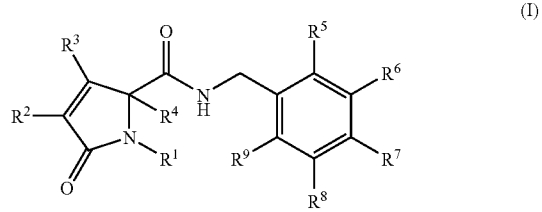

wherein:

$R^1$ represents $C_{1-6}$ alkyl, $C_{2-6}$ alkenyl, $C_{2-6}$ alkynyl, $C_{3-6}$ cycloalkyl, $C_{3-6}$ cycloalkylmethyl- or pyridinylmethyl-, any of which is optionally substituted with 1, 2 or 3 halogen atoms; or unsubstituted phenyl or benzyl; and $R^2$ represents hydrogen, halogen, $C_{1-6}$ alkyl, $C_{6-10}$ arylmethyl-, $C_{2-6}$ alkenyl, $C_{2-6}$ alkynyl or $C_{3-6}$ cycloalkylmethyl-; and any of said $C_{1-6}$ alkyl, $C_{6-10}$ arylmethyl-, $C_{2-6}$ alkenyl, $C_{2-6}$ alkynyl or $C_{3-6}$ cycloalkylmethyl- is optionally substituted with 1, 2 or 3 halogen atoms;

and $R^3$ represents hydrogen, fluorine or methyl;

or $R^2$ and $R^3$ together with the carbon atoms to which they are attached form a benzene ring optionally substituted with 1, 2 or 3 substituents, which may be the same or different, selected from the group consisting of $C_{1-6}$ alkyl, $C_{2-6}$ alkenyl and $C_{2-6}$ alkynyl;

$R^4$ represents hydrogen, fluorine or methyl; and $R^5$, $R^6$, $R^7$, $R^8$ and $R^9$ independently represent hydrogen, halogen, cyano, $C_{1-6}$ alkyl, $C_{2-6}$ alkenyl, $C_{2-6}$ alkynyl, $C_{3-6}$ cycloalkyl or phenyl, and any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms; or $R^8$ and $R^9$ together with the carbon atoms to which they are attached form a benzene ring which is optionally substituted with 1, 2 or 3 halogen atoms;

with the proviso that when $R^5$ and $R^9$ are both selected from hydrogen or fluorine, at least one of $R^6$, $R^7$ and $R^8$ is a halogen atom.

2. The compound or salt according to claim 1, wherein $R^1$ represents unsubstituted $C_{1-4}$ alkyl, $C_{3-5}$ cycloalkyl, pyridinylmethyl-, phenyl or benzyl.

3. The compound or salt according to claim 1, wherein $R^1$ represents methyl or ethyl.

4. The compound or salt according to claim 1, wherein $R^1$ represents methyl.

5. The compound or salt according to claim 1, wherein
either $R^2$ represents hydrogen or methyl and $R^3$ represents hydrogen or methyl;
or $R^2$ and $R^3$ together with the carbon atoms to which they are attached form an unsubstituted benzene ring.

6. The compound or salt according to claim 5, wherein $R^2$ and $R^3$ together with the carbon atoms to which they are attached form an unsubstituted benzene ring.

7. The compound or salt according to claim 1, wherein $R^4$ represents hydrogen or methyl.

8. The compound or salt according to claim 7, wherein $R^4$ represents hydrogen.

9. The compound or salt according to claim 1, wherein $R^5$, $R^6$, $R^7$, $R^8$ and $R^9$ independently represent hydrogen, halogen, cyano, trifluoromethyl or unsubstituted $C_{1-6}$ alkyl; or $R^8$ and $R^9$ together with the carbon atoms to which they are attached form an unsubstituted benzene ring.

10. The compound or salt according to claim 1, wherein $R^1$ represents unsubstituted $C_{1-4}$ alkyl, $C_{2-4}$ alkenyl, $C_{3-5}$ cycloalkyl, pyridinylmethyl-, phenyl or benzyl;

$R^2$ and $R^3$ represent hydrogen or methyl, or $R^2$ and $R^3$ together with the carbon atoms to which they are attached form an unsubstituted benzene ring; and $R^5$, $R^6$, $R^7$, $R^8$ and $R^9$ independently represent hydrogen, chlorine, fluorine, bromine, methyl or trifluoromethyl.

11. The compound or salt according to claim 10, wherein $R^1$ represents methyl or ethyl.

12. A compound which is:
1-cyclopropyl-N-[(2,4-dichlorophenyl)methyl]-3-methyl-5-oxo-2,5-dihydro-1H-pyrrole-2-carboxamide;
N-[(2,4-dichlorophenyl)methyl]-2-ethyl-3-oxo-2,3-dihydro-1H-isoindole-1-carboxamide;
N-[(2-chloro-4-fluorophenyl)methyl]-2-ethyl-3-oxo-2,3-dihydro-1H-isoindole-1-carboxamide; or
N-[(2-chloro-4-fluorophenyl)methyl]-2-methyl-3-oxo-2,3-dihydro-1H-isoindole-1-carboxamide.

13. The compound according to claim 1 which is N-{[2-chloro-3-(trifluoromethyl)phenyl]methyl}-2-ethyl-3-oxo-2,3-dihydro-1H-isoindole-1-carboxamide of the formula:

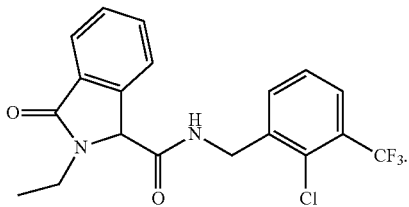

14. The compound according to claim 1 which is N-[(2,4-dichlorophenyl)methyl]-2-methyl-3-oxo-2,3-dihydro-1H-isoindole-1-carboxamide of the formula:

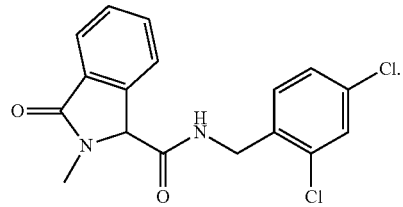

15. The compound according to claim 1 which is N-{[2-chloro-3-(trifluoromethyl)phenyl]methyl}-2-methyl-3-oxo-2,3-dihydro-1H-isoindole-1-carboxamide of the formula:

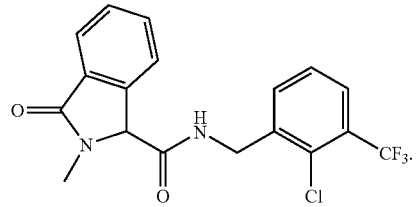

16. A pharmaceutical composition which comprises the compound or a pharmaceutically acceptable salt thereof, as defined in claim 1, and a pharmaceutically acceptable carrier or excipient.

* * * * *